US009861465B2

(12) United States Patent
Tan et al.

(10) Patent No.: US 9,861,465 B2
(45) Date of Patent: Jan. 9, 2018

(54) METHOD FOR FORMING A TISSUE CONSTRUCT AND USE THEREOF

(75) Inventors: Lay Poh Tan, Singapore (SG); Philip Wong, Singapore (SG); Yin Chiang Freddy Boey, Singapore (SG); Subbu Venkatraman, Singapore (SG)

(73) Assignee: Nanyang Technological University, Singapore (SG)

( * ) Notice: Subject to any disclaimer, the term of this patent is extended or adjusted under 35 U.S.C. 154(b) by 645 days.

(21) Appl. No.: 13/825,540

(22) PCT Filed: Sep. 22, 2011

(86) PCT No.: PCT/SG2011/000327
§ 371 (c)(1),
(2), (4) Date: Jun. 4, 2013

(87) PCT Pub. No.: WO2012/039682
PCT Pub. Date: Mar. 29, 2012

(65) Prior Publication Data
US 2013/0245784 A1    Sep. 19, 2013

Related U.S. Application Data

(60) Provisional application No. 61/385,335, filed on Sep. 22, 2010.

(51) Int. Cl.
| A61F 2/02 | (2006.01) |
| A61L 27/38 | (2006.01) |
| A61L 27/44 | (2006.01) |
| A61L 27/50 | (2006.01) |
| A61L 27/52 | (2006.01) |
| A61L 27/54 | (2006.01) |
| A61L 27/58 | (2006.01) |

(52) U.S. Cl.
CPC .......... *A61F 2/02* (2013.01); *A61L 27/3808* (2013.01); *A61L 27/3826* (2013.01); *A61L 27/3834* (2013.01); *A61L 27/44* (2013.01); *A61L 27/507* (2013.01); *A61L 27/52* (2013.01); *A61L 27/54* (2013.01); *A61L 27/58* (2013.01); *A61L 2300/62* (2013.01); *A61L 2300/64* (2013.01); *A61L 2400/18* (2013.01)

(58) Field of Classification Search
CPC ......... A61F 2/02; A61L 27/50; B32B 37/025; B32B 38/10
See application file for complete search history.

(56) References Cited

U.S. PATENT DOCUMENTS

| 5,833,641 | A | 11/1998 | Curtis et al. |
| 6,428,802 | B1 | 8/2002 | Atala |
| 6,767,928 | B1 * | 7/2004 | Murphy et al. ............... 521/51 |
| 6,995,013 | B2 | 2/2006 | Connelly et al. |
| 7,524,335 | B2 | 4/2009 | Slivka et al. |
| 7,579,189 | B2 | 8/2009 | Freyman et al. |
| 2006/0141617 | A1 | 6/2006 | Desai et al. |

(Continued)

*Primary Examiner* — Victor Nguyen
(74) *Attorney, Agent, or Firm* — Seed IP Law Group LLP

(57) ABSTRACT

The present invention relates to a method for forming a tissue construct having a composite structure. The method includes providing a biodegradable substrate, wherein the substrate is adapted to allow deposition or growth of a plurality of cells; providing a vascularized layer comprising a plurality of blood vessels therein; and adhering the vascularized layer to the substrate.

13 Claims, 10 Drawing Sheets

(56) References Cited

U.S. PATENT DOCUMENTS

| | | |
|---|---|---|
| 2006/0159722 A1 | 7/2006 | Braithwaite et al. |
| 2007/0299510 A1* | 12/2007 | Venkatraman ........ A61F 2/0077 623/1.44 |
| 2009/0069893 A1 | 3/2009 | Paukshto et al. |
| 2009/0248145 A1 | 10/2009 | Chan et al. |

* cited by examiner (A)

(B)

METHOD FOR FORMING A TISSUE CONSTRUCT AND USE THEREOF

CROSS-REFERENCE TO RELATED APPLICATION

This application claims the benefit of priority of U.S. Provisional Patent Application No. 61/385,335, filed 22 Sep. 2010, the contents of which being hereby incorporated by reference in its entirety for all purposes.

TECHNICAL FIELD

The invention relates generally to tissue constructs for repairing tissues. In particular, the invention relates to a method for forming a tissue construct having a composite structure.

BACKGROUND

Commonly used approaches to the reconstruction of defective organs and/or tissues include cell therapy and tissue engineering. Cell therapy involves injecting cells directly into the part of the damaged tissue for repair. Problems associated with this approach include low cell density and low cell survival rate.

The major aspect of tissue engineering is the design and fabrication of constructs for the replacement of non-functional or damaged tissue. A general method of engineering tissues in vitro is the use of a scaffold, in or on which cells are grown. A respective scaffold should be biodegradable before or after implantation. Problems associated with this approach include nutrient and waste transport issues due to the high thickness of the scaffolds required coupled with a lack of cellular orientation especially in regenerating tissues that are anisotropic in nature, for example muscle tissues.

Culturing the tissue in vitro followed by subsequent implantation of the tissue into the body may overcome the issues of low cell density. Nonetheless, the problem of limited nutrient and waste transport remains a challenge.

Therefore, there remains a need to provide for a tissue construct that overcomes, or at least alleviates, the above problems.

SUMMARY

According to one aspect of the invention, there is provided a method for forming a tissue construct having a composite structure. The method includes:
(a) providing a biodegradable substrate, wherein the substrate is adapted to allow deposition or growth of a plurality of cells;
(b) providing a vascularized layer comprising a plurality of blood vessels therein; and
(c) adhering the vascularized layer to the substrate.

In another aspect, the invention relates to a tissue construct having a composite structure. The tissue construct includes:
(a) a biodegradable substrate, wherein the substrate is adapted to allow deposition or growth of a plurality of cells; and
(b) a vascularized layer comprising a plurality of blood vessels therein.

In a further aspect, use of the tissue construct for the growth and structuring of new tissue, or for the repair of damaged tissue is provided.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

The present invention lies in the field of implantable biological prostheses, particularly tissue constructs made in vitro with subsequent implantation in vivo. It involves the creation of composite tissue constructs with multi-functions. The constructs are developed for the replacement of tissues that are generally anisotropic in nature. Substrates of the composite tissue constructs are made of biodegradable polymers that will eventually degrade leaving behind the tissues that are to be integrated with the host organs.

Figure 1:
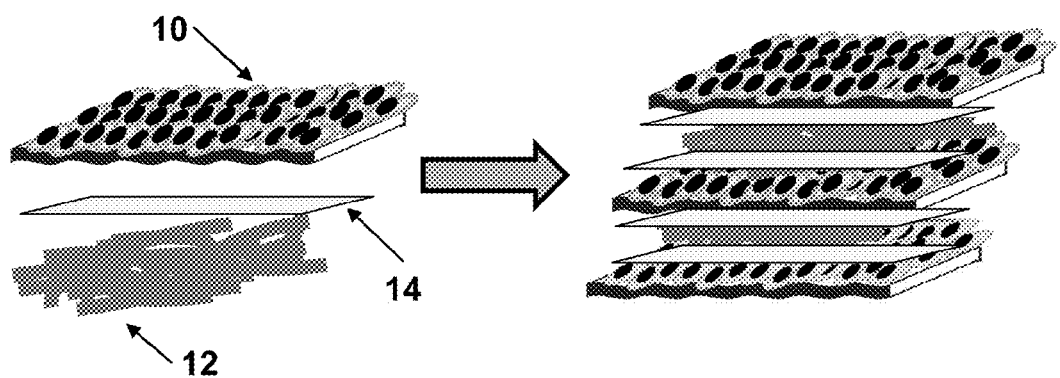
FIG. 1 shows a tissue construct formed by (A) adhering a substrate to a vascularized layer via an intermediate layer, and (B) adhering a substrate to a vascularized layer by suturing.
Figure 1:
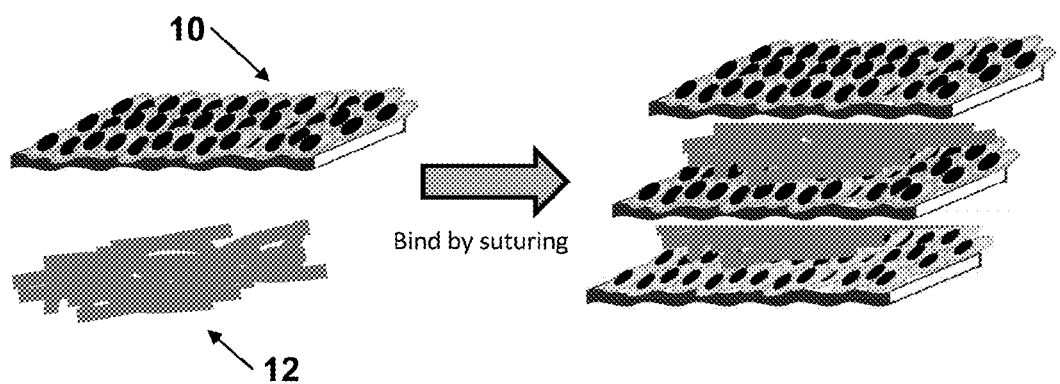

In one aspect of the invention, there is disclosed a method for forming a tissue construct having a composite structure as illustrated in FIGS. 1A and 1B. The method includes providing a biodegradable substrate 10, wherein the substrate 10 is adapted to allow deposition or growth of a plurality of cells. The method also includes providing a vascularized layer 12 comprising a plurality of blood vessels therein. The method further includes adhering the vascularized layer 12 to the substrate 10.

The term "composite structure" as used in the present invention means any structure made of at least two layers, i.e. two, three, four, five or more consecutive layers layered or arranged on each other. Each of these layers may be a substantially flat sheet.

The tissue construct may be configured to have any suitable shape as long as it is relatively flat and sufficiently pliable to allow a surgeon to manipulate the shape of the tissue construct to conform to the anatomical site of interest and to be sutured or stapled thereto. The outline and the size of the tissue construct may vary according to the surgical application as would be apparent to one of skill in the art. The tissue construct can be pre-shaped or shaped by the surgeon during the surgical procedure. To be sufficiently moldable during implantation, the tissue construct can be substantially flexible along its longitudinal axis (longitudinal axis in this respect means the main axis or the main longitudinal extension) of the tissue construct.

The tissue construct described herein can be used for implantation in mammals (such as a human, dog, cat, rabbit, mouse, rat, etc.) in need thereof. Especially, the tissue construct can be used for treating any wall defect or damaged organ, but is not limited thereto. Various examples of wall defects are hernia defects, anatomical defects of the abdominal wall, diaphragm and/or chest wall, or defects in the genitourinary system. Various examples of damaged organs which can be treated, for example, by winding the sheet-like tissue construct around the damaged organ or implanting it into the wall of the damaged organ for reinforcing it, include internal organs such as the spleen, liver, kidney, lung, bladder or heart, or organs of the intestinal tract, such as the stomach or the bowel. Illustrative example of a tissue construct described herein includes heart patches.

The layer thickness of each of the layers of the composite structure can be specifically adjusted in view of the respective mechanical or physical properties of each of the layers. However, the thickness of each of the layers is generally in the micrometer range, for example, the thickness is in the range of about 10 to about 500 µm (microns). The layer should preferably not be thicker than about 1,000 µm. Especially, if the overall thickness of the tissue construct is too high, the flexibility will generally be so low that the tissue construct cannot be adequately anchored to the surrounding tissue, while being able to flexibly and elastically stretch along with the tissue. The lower limit of each of the layers should be about 10, 15, 20, 25, 50, or 100 µm in order to provide enough burst strength to the tissue construct of the invention. Each layer can have a thickness in the above-mentioned range or can have a varying thickness within this range.

Figure 8:
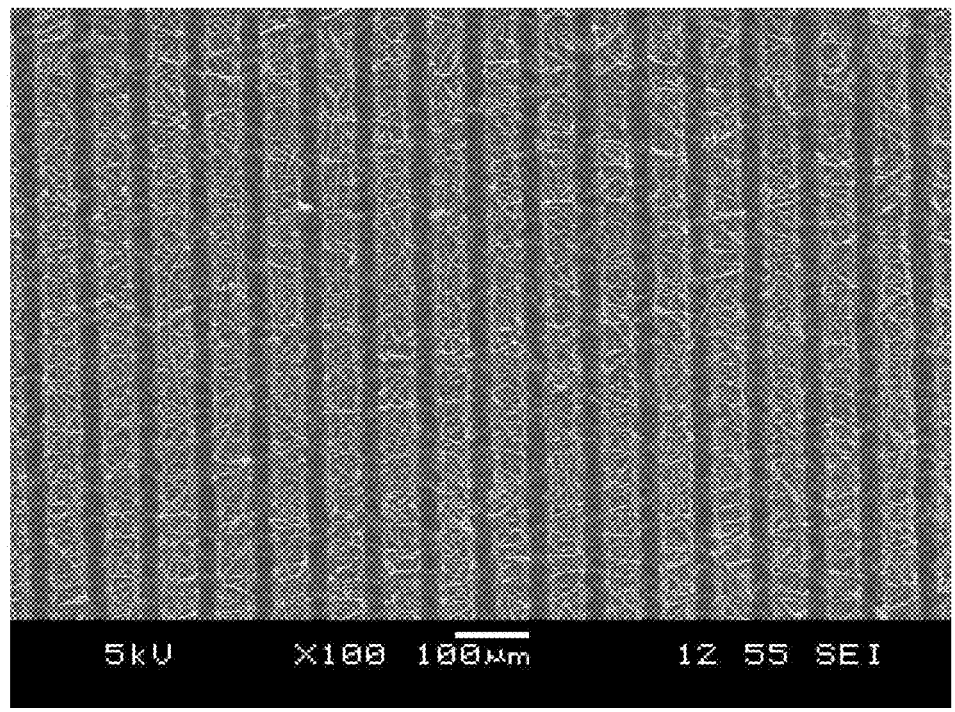
FIG. 8 shows (A) channels on fibre-spun substrate and (B) magnified version showing channels on fibre-spun substrate to increase porosity of scaffold. The fibre diameter of the top layer is 0.6 micron and the bottom layer 2 micron.
Figure 8:
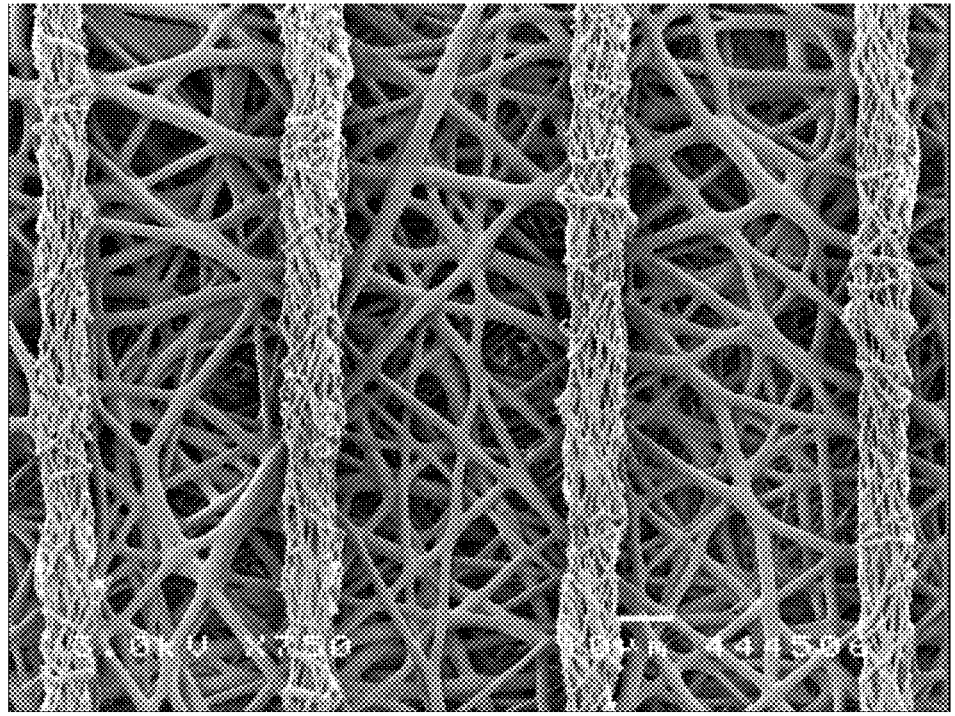

Any substrate may be used in the method of the invention as long as it provides a suitable surface and environment for the deposition or growth of cells. In various embodiments, the substrate may be patterned to form a plurality of regions for the deposition or growth of cells. For example, the substrate may be a solid material that is patterned to form a plurality of channels of desired dimensions (see below). The substrate can also be a mat of fibres that are subsequently patterned to form a plurality of channels of desired dimensions (FIGS. 8A and 8B).

The substrate includes or consists of a biodegradable material, such as a biodegradable polymer. A biodegradable material is readily susceptible to biological processing in vivo. It can be degraded by a living organism or a part thereof (e.g., bacterial or enzymatic action) or by the impact of the ambience, such as exposure to light, moisture, elevated temperature and/or air. Degradation of a biodegradable material may result in the formation of primary degradation products such as compounds of low molecular weight, which then decay further through the action of a living organism. In the context of the present invention, the term "biodegradable material" particularly refers to matter that can be completely removed from a localized area, by physiological metabolic processes. A "biodegradable" compound can, when taken up by a cell, be broken down into components by cellular machinery such as lysosomes or by hydrolysis that the cells can either reuse or dispose of without significant toxic effect on the cells. Examples of biodegradation processes include enzymatic and non-enzymatic hydrolysis, oxidation and reduction. Suitable conditions for non-enzymatic hydrolysis, for example, include exposure of biodegradable material to water at a temperature and a pH of a lysosome (i.e. the intracellular organelle). The degradation fragments typically induce no or little organ or cell overload or pathological processes caused by such overload or other adverse effects in vivo.

Various examples of biodegradable materials are known in the art, any of which are generally suitable for use in the method of the present invention. As some illustrations of polymers that are considered to be biodegradable may serve: a polyglycolide, a polylactide, a polycaprolactone, a polyamide, a biodegradable aliphatic polyester, and/or copolymers thereof, with and without additives (e.g. calcium phosphate glass), and/or other copolymers (e.g. poly(caprolactone lactide), a poly(ester amide), a poly(amino acid), a pseudo-poly(amino acid) such as a poly(iminocarbonate-amide) copolymer, poly(lactide glycolide), poly(lactic acid ethylene glycol)), poly(ethylene glycol), poly(ethylene glycol) diacrylate, a polyalkylene succinate, polybutylene diglycolate, a polyhydroxybutyrate, polyhydroxyvalerate, a polyhydroxybutyrate/polyhydroxyvalerate copolymer; poly (hydroxybutyrate-co-valerate); a polyhy-droxyalkaoates, a poly(caprolactone-polyethylene glycol) copolymer, poly (valerolactone), a polyanhydride, a poly(orthoester) and/or a blend with a polyanhydride, poly(anhydride-co-imide), an aliphatic polycarbonate, a poly(propylene carbonate), a poly(hydroxyl-ester), a polydioxanone, a polyanhydride ester, a polycyanoacrylate, a poly(alkyl cyanoacrylate), a poly(amino acid), a poly(phosphazene), a poly(propylene fumarate), poly(propylene fumarate-co-ethylene glycol), a poly(fumarate anhydride), fibrinogen, fibrin, gelatin, cellulose, a cellulose derivative, chitosan, a chitosan derivative such as chitosan NOCC, chitosan NOOC-G or NO-carboxymethyl chitosan NOCC, alginate, a polysaccharide, starch, amylase, collagen, a polycarboxylic acid, a poly(ethyl ester-co-carboxylate carbonate), poly(iminocarbonate), poly(bisphenol A-iminocarbonate), poly(trimethylene carbonate), poly(ethylene oxide), poly(epsilon-caprolactone-dimethyltrimethylene carbonate), a poly(alkylene oxalate), poly(alkylcarbonate), poly(adipic anhydride), a nylon copolyamide, carboxymethyl cellulose; copoly(ether-esters) such as a PEO/PLA dextran, a biodegradable polyester, a biodegradable polyether, a polydihydropyran, a biodegradable polyketal such as poly (hydroxylmethylethylene di(hydroxymethyl) ketal) or poly [1-hydroxymethyl-1-(2-hydroxy-1-hydroxymethyl-ethoxy)-ethylene oxide], a polydepsipeptide, a polyarylate (L-tyrosine-derived) and/or a free acid polyarylate, a poly(propylene fumarate-co-ethylene glycol) such as a fumarate anhydride, a hyaluronate, poly-p-dioxanone, a polyphosphoester, polyphosphoester urethane, a polysaccharide, starch, rayon, rayon triacetate, latex, and/or copolymers, blends, and composites of any of the above.

Figure 2:
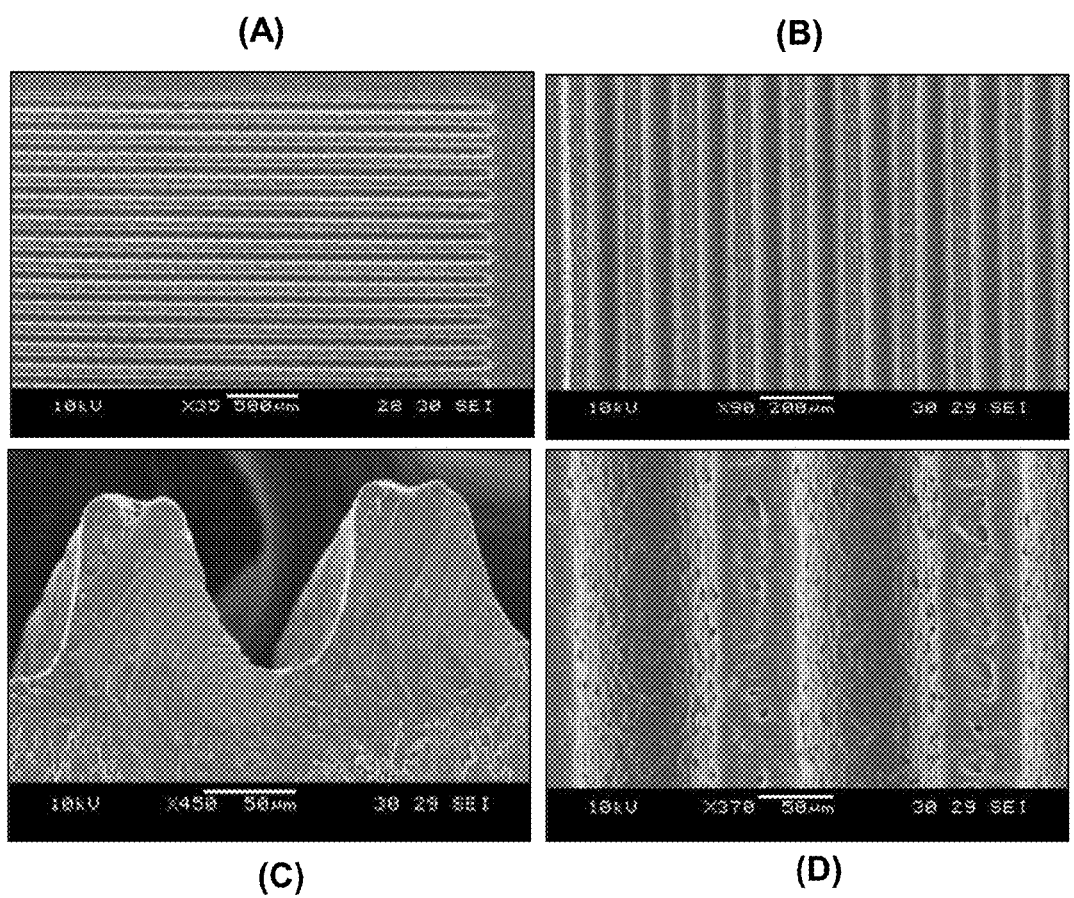
FIG. 2 shows the topology of microchannels fabricated directly using femtosecond laser on biodegradable PLLA-PCL film. (a, b) Highly repeatable structure was achieved at consistent interval distance. (c) Cross section of scaffold showing U-shape channel morphology. (d) Consistent channels with highly repeatable channel width and interval distance.
Figure 3:
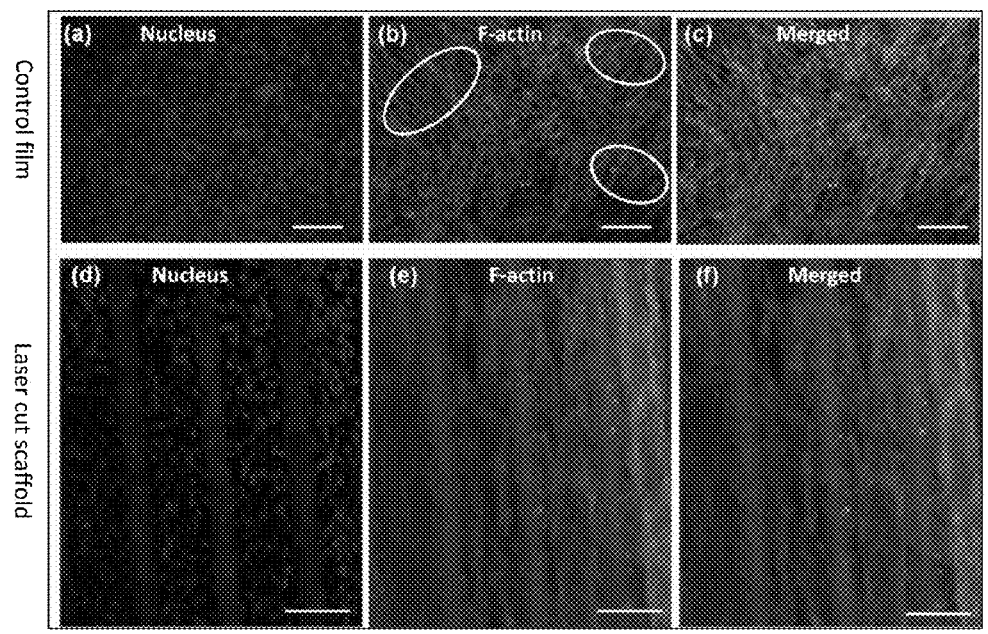
FIG. 3 shows the fluorescence images showing alignment of confluence cell patch on (a-c) control scaffold and (d-f) microchannel scaffold after 4 days of cell culture. Cells were stained to reveal nucleus in blue (a, d) and F-actin in red (b, e). (a-c) Cells grown on flat polymer surface showed localized alignment in random direction as indicated by circles on image. (d-f) Confluence cell patch inside microchannels showed continuous alignment to the channel direction. Scale bar=100 μm.
Figure 4:
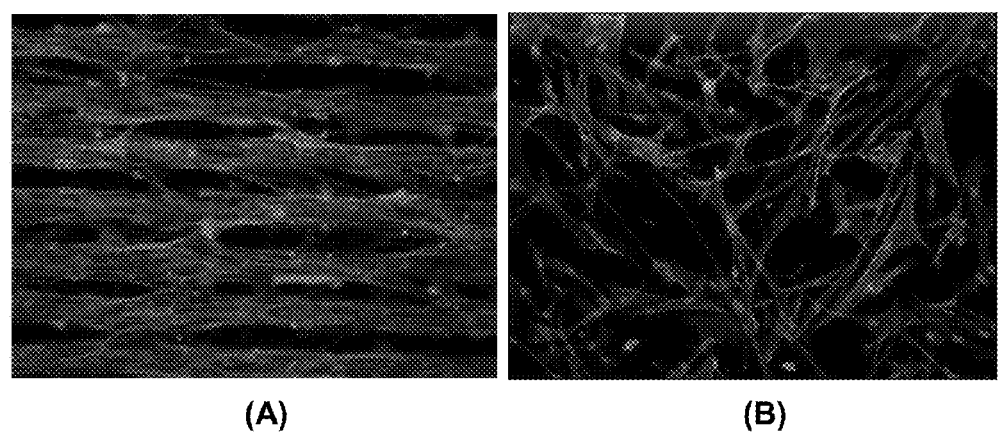
FIG. 4 shows the fluorescence images of human smooth muscle cells on (A) laser-cut substrate and (B) flat substrate. The blue dye shows the nucleus and red dye the F-actin. The laser-cut substrate again demonstrates that it could guide the cells to align in the direction of the channels.
Figure 5:
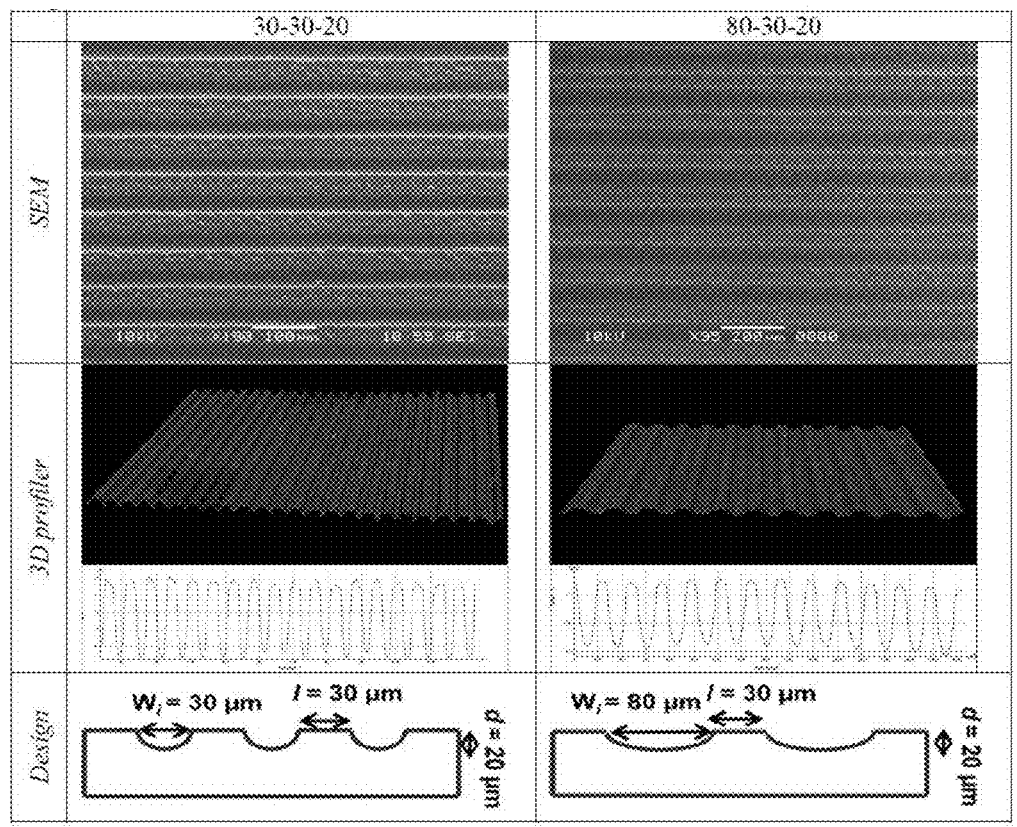
FIG. 5 shows the topography of channels fabricated directly using femtosecond laser on biodegradable PLLA-PCL film, with sinusoidal surface topology inside the channels (SEM & 3D profiler).

The substrate may be of any substantially flat geometry (with or without micropores in the substrate, e.g. the fibre-spun substrate). The channel may be located anywhere on the substrate. Where a plurality of channels is provided on the substrate, they may be located at any position relative to each other and in any orientation with respect to each other. In some embodiments at least some channels run parallel to each other. Such parallel channels may for instance be adjacent or contiguous to each other. In one embodiment adjacent channels share a common lateral wall. In some embodiments the channel includes a branching. The channel may be defined by at least a pair of opposing lateral walls and a base, such as base wall (as illustrated in FIG. 2 and FIG. 5). The distance between the two opposing lateral walls of at least one portion of the channel (or of the entire channel) is within the micrometer range. As used herein, the term micrometer range refers to a range of between 1 µm and 1,000 µm (microns). The walls of the channel may be of any desired internal surface characteristics and any desired material as long as they allow cells of a desired type to grow therein. Furthermore, different internal areas of the walls of the channel may provide different surface characteristics and include or consist of different materials. In typical embodiments the channel is open along its length in that it defines a trench (as opposed to a sub-surface channel). The channel may span (e.g. laterally, diagonally etc.) the entire length/width of the substrate. As an illustrative example, channels ranging from about 10 µm to about 200 µm in length, such as e.g. about 60 µm to about 200 µm, have been found to be well suited for growing cell line smooth muscle cells. For primary smooth muscle cells, ranges from about 50 µm to about 400 µm, such as e.g. about 60 µm to about 400 µm or about 50 µm to about 300 µm, are well suited.

As noted above, the substrate includes a surface on which selected cells can be deposited or grown. For this purpose the surface properties of the substrate, including any channel present, may be altered where required. The respective surface, or a part thereof, may for instance be altered by means of a treatment carried out to alter characteristics of the solid surface. Such a treatment may include various means, such as mechanical, thermal, electrical or chemical means. As an illustrative example, the surface properties of any hydrophobic surface can be rendered hydrophilic by coating with a hydrophilic polymer or by treatment with surfactants. Examples of a chemical surface treatment include, but are not limited to exposure to hexamethyldisilazane, trimethylchlorosilane, dimethyldichlorosilane, propyltrichlorosilane, tetraethoxysilane, glycidoxypropyltrimethoxy silane, 3-aminopropyl-triethoxysilane, 2-(3,4-epoxy cyclohexyl) ethyltrimethoxysilane, 3-(2,3-epoxy propoxyl)propyltrimethoxysilane, or 2,3-epoxy-1-propanol. A surface treatment may also include applying a coating of a peptide, a polypeptide or a protein (such as a cell surface protein), for instance fibronection, vitronectin, laminin, collagen, gelatine, polylysine or the synthetic peptides arginine-glycine-aspartate (RGD) and tyrosine-isoleucine-glycine-serine-arginine (YIGSR). A large number of biodegradable polymers, such as poly(glycolic acid), poly(L-lactic acid) or poly(lactic-co-glycolic acid) (see also above) are also known to be suitable for a surface treatment to facilitate cell adhesion.

A plurality of cells may be deposited or grown or seeded on the substrate surface, for example, in the channel patterned on the substrate surface. The cells may be seeded by any means. They may for example be dispensed on top of the channel by means of a pipette. Any cell may generally be selected to be seeded into the channel. Examples of respective cells include, but are not limited to, smooth muscle cells, skeletal muscle cells, endothelial cells, stem cells, progenitor cells, myocytes, bone marrow cells, neurons, pericytes and fibroblasts. Cells used in the method of the present invention may be of any source. They may for example be native cells, including cells isolated from tissue, or they may be cells of a cell line. Respective cells may also be modified, e.g. treated by an enzyme, exposed to radiation, transformed by the incorporation of heterologous matter (an organelle, genetic material, inorganic matter etc.), or they may be recombinant or transgenic. The cells may be seeded at any density, as long as they are able to proliferate on the base of the channel(s) and as long as they are seeded below confluence. Seeding densities as low as $1\times10^4$ cells/cm$^2$ were found suitable for smooth muscle cells. The cells are allowed to adhere to the base of the channel and to proliferate. Depending on the cells used, they are allowed to proliferate up to a density of about 80% to about 100%, such as about 85%, 90% or 95%. The cells are allowed to proliferate near to confluence or, in other words, allowed to reach, at least substantially, confluence at the base of the channel. The term "confluence" is used herein—unless stated otherwise—in the regular meaning to describe a state in which cells have grown within a certain amount of space.

At this point surface to surface contact with other cells causes the individual cells to inhibit their growth. In line with this meaning of the term "confluence", the expression "proliferate near to confluence" or "reach at least substantially confluence means that the majority of cells (say for example, 70%, 80%, 90%, 95%, 98% or 99% of the cells) have grown to an extent that this majority of cells contact at least one neighboring cell such that the growth of the individual cells of the majority of cells is inhibited by contact inhibition. This means that is not necessary that all cells only a majority of the cells proliferate to confluence. During proliferation the cells align unidirectionally. Smooth muscle cells show an aligned and elongated morphology in a direction that is at least essentially parallel to the closest lateral wall of the channel, which is typically the direction that corresponds to the length of the channel(s). Accordingly, by pre-selecting a design of the channel, and in particular the walls thereof, a "tissue axis" may be defined. This may be particularly helpful in embodiments where a tissue graft is to be formed from the cells and/or the biodegradable substrate in an aligned fashion (anisotropic properties). This two-dimensional alignment and elongation occurs in the presence of the channel wall and does not require any further factors. The channel walls provide contact guidance cues and/or mechanical cues, thereby causing the cells to align, and in a number of embodiments to show an elongated morphology.

As decribed above, cells may be directed to orientate, for example, in the longitudinal direction by having a plurality of regions patterned on the substrate surface. These regions can be created using micro-contact printing of extracellular matrix (ECM) proteins, e.g. fibronection, laminin, and collagen. The regions can be 2D lanes in the longitudinal direction whose height dimensions are negligible compared to the thickness of the substrate. The regions can also be 3D channels that are patterned in the longitudinal direction. These channels can be patterned using laser-cutting or lithography methods. The regions can also be created using fibre-spinning method where the fibres are oriented in the longitudinal direction that form grooves acting as guidance cues for the cell alignment.

As illustrative embodiments, for 2D lanes using ECM proteins, the dimension of the lanes may be in the range of 10 to 50 microns with an interval of 10 to 50 microns intervals. For 3D channels, the trench may have a depth and width that ranges from 10 to 100 microns. The interval between the channels may be in the range of 20 to 50 microns. For fibre-spinning, the fibre diameter may be in the range of 0.2 to 200 microns and fibres may be arranged closely without any gap therebetween. The thickness of the substrate may be in the range of 10 to 500 microns, such as 10 to 100 microns.

Patterning on the substrate may for example be formed by micro-contacting, laser-cutting, lithography, or fibre-spinning. In one embodiment, 3D channels may be formed on the substrate by laser-cutting. Femtosecond laser may be employed for the laser-cutting, for example. The femtosecond laser beam is focused by an optical focus lens. With the right choice of pulse energy, the laser beam can be directly focused on the substrate surface to induce polymer ablation. Two targeted microchannel sizes were produced via laser-cutting: 30 µm width, 30 µm interval, 20 µm depth (30-30-20) and 80 µm width, 30 µm interval, 20 µm depth (80-30-20), (see Examples described below).

In an alternative embodiment, fibre-spinning or electro-spinning is used to induce cellular alignment. Electrospinning process uses the principle of electrostatic field to form and accelerate the liquid jet from the tip of a capillary to the collector. When an electric field is applied between the polymeric melt or solution contained in a syringe and collector, charges accumulate and are forced to the surface of an emerging polymer droplet at the needle tip. When the applied electrostatic field is stronger than the surface tension of the solution, Taylor cone is formed and a continuous jet is attracted toward a conductive grounded collector. As the electrically charged jet moves toward the collector, it is elongated by the electrostatic interactions between the charges on the same jet. Meanwhile, the solvent evaporates and the polymer jet solidified into fibers. A plurality of fibres are then deposited onto the substrate surface and depending on the collector configuration, the fibers could be arranged randomly or aligned in the longitudinal direction to form grooves acting as guidance cues for the cell alignment, as mentioned above.

In vivo, cells reside within environments in close proximity to blood vessels that supply tissues with the necessary nutrients and oxygen, as well as remove from tissues waste products and carbon dioxide. To facilitate nutrients and waste transport across the tissue construct, it is proposed by the present inventors to include a vascularized layer in the tissue construct. Although spontaneous vascular in-growth can occur after implantation due to the inflammatory wound healing response, the process occurs at a slow rate of several tenths of microns per day and the functional capillary density at the center of the tissue construct is less than that at the border zone.

Figure 9:
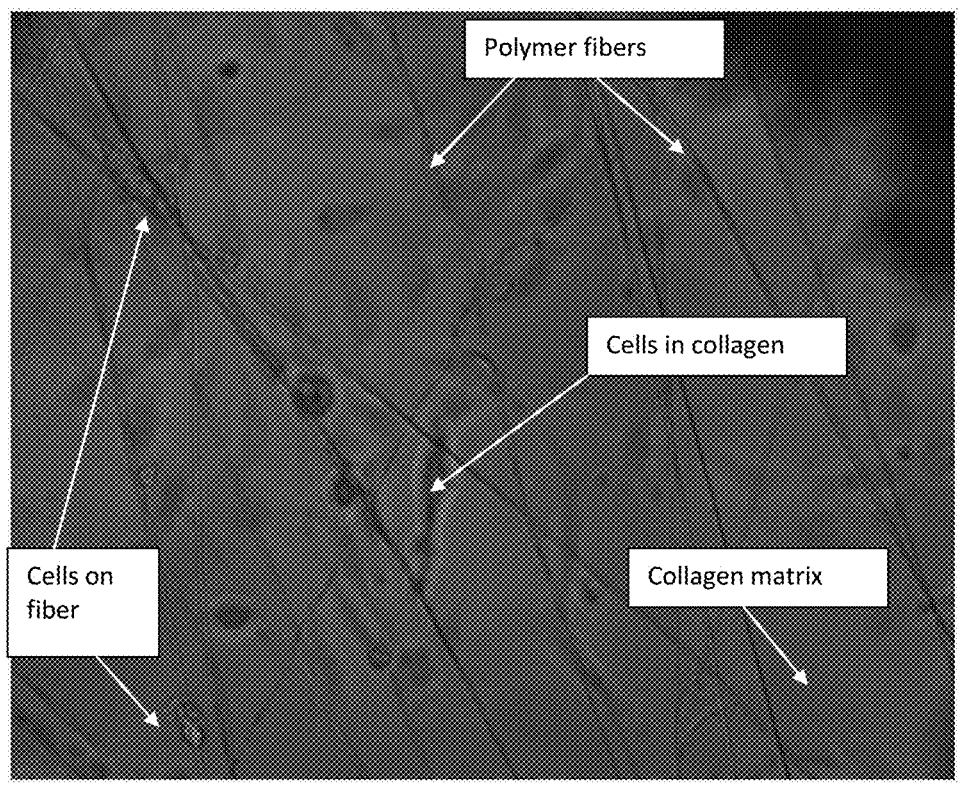
FIG. 9 shows the fibre network embedded in the collagen gel for support. The collagen concentration of 1.5 mg/ml was used giving a corresponding modulus of about 100 Pa. VEGF at 100 ng/ml was added into the collagen. The fibers have a diameter of 9-10 microns.

The vascularized layer serves to facilitate transportation of oxygen, nutrients and waste as well as to promote angiogenesis. In various embodiments, the vascularized layer includes a plurality of blood vessels therein. The blood vessels may be formed by a network of degrading or almost fully degraded fibres (biodegradable fibres) encapsulated with or wrapped around by endothelial cells, for example. Suitable cells may include also smooth muscle cells, microvascular endothelial cells, stem cells, and combination thereof. The fibres may be obtained from fibre-spinning or melt-spinning. The fibre thus obtained may have diameters in the range of 0.5 to 50 microns. The fibres are initially cultured with endothelial cells in the presence of growth factors such as a vascular endothelial growth factor (VEGF) medium to aid in the formation of blood vessels. The fibers may also be embedded in a hydrogel (for example, collagen or other synthetic gels that support cell growth) for additional support of vessel network (see FIG. 9). The endothelial cells wrap around the fibres, eventually forming a highly encapsulated fibrous structure. The polymer of the fibres is subsequently allowed to degrade, leaving behind a hollow tube made up of endothelial cells. In various embodiments, the biodegradable polymer used for forming the fibres include polymers having rapid degrading rate, such as poly(lactide glycolide) (PLGA 50/50 (by composition)).

Figure 10:
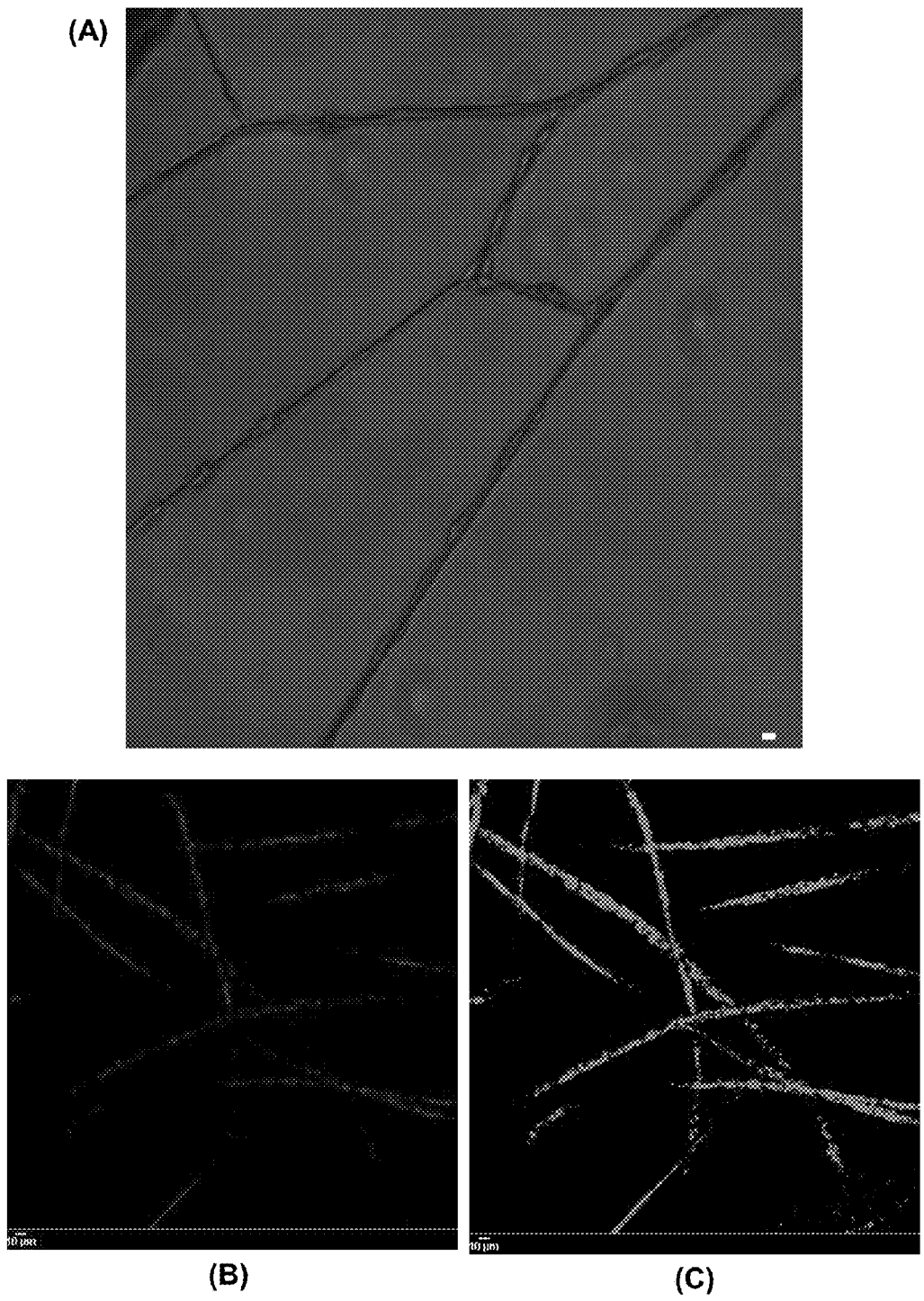
FIG. 10 shows (A) the bright field picture of HUVEC cells growing and encapsulating the polymer fibers after 7 days of culture; (B) the fluorescence image of the green dye (DiO) showing the network of PLGA polymer fibres; (C) the fluorescence image of the red dye (cell tracker DiL) showing HUVEC cells proliferating on the polymer fibers after 7 days of culture.

FIG. 10 shows (A) the bright field picture of Human Umbilical Vein Endothelial Cells (HUVEC) cells growing and encapsulating the polymer fibers after 7 days of culture; (B) the fluorescence image of the green dye (DiO) showing the network of PLGA polymer fibres; (C) the fluorescence image of the red dye (cell tracker DiL) showing HUVEC cells proliferating on the polymer fibers after 7 days of culture.

As illustrated in FIG. 1A, the substrate 10 may be adhered to the vascularized layer 12 via an intermediate layer 14. The intermediate layer 14 may be formed of gelatin, collagen or fibrin. A thin layer of less than 10 microns may be used for the intermediate layer 14. Besides serving as an adhesion layer between the substrate 10 and the vascularized layer 12, the intermediate layer 14 at the same time provides an ECM like environment for the cells.

The term "extracellular matrix" refers to a substance existing between somatic cells such as epithelial cells. In vivo the extracellular matrix is matter located outside of cells of a multicellular organism. Extracellular matrices are typically produced by cells, and therefore, are biological materials. Extracellular matrices are involved in supporting tissue as well as in internal environmental structure essential for survival of all somatic cells. A respective matrix can also be formed or transferred in vitro and ex vivo. Extracellular matrices are generally produced from connective tissue cells. Some extracellular matrices are secreted from cells possessing basal membrane, such as epithelial cells or endothelial cells. Extracellular matrices are roughly divided into fibrous components and matrices filling there between. Fibrous components include collagen fibers and elastic fibers. A basic component of matrices is a glycosaminoglycan (acidic mucopolysaccharide), most of which is bound to non-collagenous protein to form a polymer of a proteoglycan (acidic mucopolysaccharide-protein complex). In addition, matrices include glycoproteins, such as laminin of basal membrane, microfibrils around elastic fibers, fibers, fibronectins on cell surfaces, and the like. Particularly differentiated tissue has the same basic structure. For example, in hyaline cartilage, chondroblasts characteristically produce a large amount of cartilage matrices including proteoglycans. In bones, osteoblasts produce bone matrices which cause calcification. Examples of proteins associated with an extracellular matrix, i.e. proteins found within an extracellular matrix of tissues, include, but are not limited to, elastin, vitronectin, fibronectin, laminin, collagen type I, collagen type III, collagen type V, collagen type VI, and proteoglycans (for example, decolin, byglican, fibromodulin, lumican, hyaluronic acid).

In an alternative embodiment, an intermediate layer adhering the substrate 10 to the vascularized layer 12 may be absent. The substrate 10 may be sutured to the vascularized layer 12 via suture threads, for example (see FIG. 1B).

In summary, high cell density is required to achieve both growth and structuring of new tissue in pre-existing tissue. Anisotropic properties are due to specific orientation of cells in native tissues. Cells in some native tissues such as skeletal muscle and cardiac muscles are not randomly organized. For the organs to function, the cells are arranged in such a way that there is anisotropic property and are oriented in certain directions. The orientation of cells in specific direction is crucial in order for it to function as an organ. In order to increase cell density, the construct ought to have certain thickness. The present invention provides for a layered composite of cells with scaffolds that have high cell density. The multi-layered tissue constructs therefore possess anisotropic properties that mimics the native tissues. To facilitate nutrients and waste transport across the tissue construct, the substrate used may have porous stuctures (example of the fibre-spun substrate) and more importantly a vascularised layer has been incorporated into the tissue construct. Although spontaneous vascular in-growth can occur after implantation due to the inflammatory wound healing response, the process occurs at a slow rate of several tenths of microns per day. By possessing high cell density with anisotropic properties and at the same time vascularization in the tissue construct itself could increase survival rate of the cells and consequently the present tissue construct could promote faster and more effective tissue repair.

In order that the invention may be readily understood and put into practical effect, particular embodiments will now be described by way of the following non-limiting examples.

EXAMPLES

Materials and Methods
Preparation of poly(L-lactide-co-ε-caprolactone) (PLLA-PCL) Film Poly(L-lactide-co-ε-caprolactone) (PLLA-PCL) film were fabricated by the solvent casting method. The block copolymer PLLA-PCL (70:30), comprised of 70% L-lactide and 30% ε-caprolactone, was used (Purac Biomaterials, Lincolnshire, Ill.). The copolymer PLLA-PCL granules were dissolved in dichloromethane (Tedia, Fairfield, Ohio) in 1:5 mass/volume ratio to achieve an optimal viscosity that is suitable for solvent casting process. The films were cast using an industrial film applicator (Paul N. Gardner Company, Inc., Sheen automatic film applicator, Florida, USA). The polymer films were dried in 37° C. vacuum oven for 7 days. The thickness of the dry cast films were approximately 100 μm.

Direct Laser Machining of Polymer

The micropatterning of the biopolymer film was carried out using a Ti-sapphire (Clark-MXR CPA 2001, Dexter, Mich.) infrared solid-state laser with a chirped pulse amplifier to produce high-intensity pulses, with the following technical specifications: pulse duration =150 fs; central wavelength=800 nm; maximum power=800 mW; fixed repetition rate=1 kHz. The laser pulse energy is adjusted by an attenuator. The femtosecond laser beam is focused by an optical focus lens. With the right choice of pulse energy, the laser beam can directly focused on the substrate surface and induce the polymer ablation. Two targeted microchannel sizes were produced: 30 μm width, 30 μm interval, 20 μm depth (30-30-20) and 80 μm width, 30 μm interval, 20 μm depth (80-30-20).

Characterization of Polymer Films

The surface morphology of the microchannel scaffold was observed using SEM performed on gold-sputtered samples (Jeol JSM-5800, Tokyo, Japan). After coating, the samples were viewed under Jeol JSM-6360LV scanning electron microscope. Alicona InfiniteFocus was employed to generate 3D structure for surface analysis. The sample was placed onto the motorized stage and was illuminated with light. Objective lens with 10× magnification was selected. The distance between the sample and the objective was adjusted to focus the image of the structure. Once the image was focused, upper limit and lower limit of the structure surface (in the software) were set to generate the 3D structure surface. The profile of the surface and its particular roughness could be obtained via the 3D structure. Attenuated Total Reflectance Fourier Transform Infrared (ATR-FTIR) spectroscopic analysis of PLLA-PCL substrates before and laser machining were performed on PerkinElmer Spectrum GX at a range of 600-4000 $cm^{-1}$. All spectra were calculated means from 8 scans at a resolution of 2 $cm^{-1}$ with correction for atmospheric water and carbon dioxide. The surface chemical composition of substrates was measured by X-ray photoelectron spectroscopy using a VG ESCALAB 250 spectrometer (Thermo Electron, U.K.). All The binding energies were corrected by referencing the binding energy of C 1s in the C-H group to 285.0 eV.

Cell Culture

Human mesenchymal stem cells (hMSCs) and cell culture medium were both obtained from Lonza (Cambrex, UK). hMSCs were expanded and cultured in mesenchymal stem cell basal medium according to the vendor's instruction. For the experiments, the cells were cultured with low-glucose Dulbecco's Modified Eagle's Medium (DMEM) containing L-glutamine (Sigma Aldrich, USA) supplemented with 10% FBS (PAA, Pasching, Austria) and 1% antibiotic/antimycotic solution (PAA, Pasching, Austria), at 37° C. in a humidified atmosphere of 5% $CO_2$. Culture medium was changed every 2-3 days. PBS and 0.05% trypsin-EDTA obtained from Invitrogen were used for washing and cell detachment purposes respectively. Scaffolds were sterilized using 70% ethanol for 30 min. Then scaffolds were washed with deionized water and PBS three times for 15 min each time. Before cell seeding, the scaffolds were immersed into the culture medium for 30 min.

Immunocytochemistry and Microscopy

Briefly, cells were fixed with 4% paraformaldehyde for 15-20 minutes and then permeabilized with 0.1% Triton X-100 for 5 min and followed by blocking with 5% bovine serum albumin (BSA) (Invitrogen) or 5% goat serum (Sigma). The primary antibodies used to target interested proteins were: rabbit polyclonal anti fibronectin (1:400) (Sigma), chicken polyclonal anti MAP2 (1:10000, Abcam) and mouse monoclonal anti heavy chain cardiac myosin (1:200) (Abcam). Secondary antibodies were Cy3 goat anti rabbit IgG (1:400, Millipore), Alexa Fluor® 568 goat anti-chicken (1:400, Molecular probes), and Alexa Fluor® 488 goat anti-mouse (1:400, Molecular probes). C2C12 myoblast and neural stem cell were used as positive controls for MHC and MAP2, respectively. Negative controls in the absence of primary antibodies were also performed. F-actin was stained with TRITC conjugated phalliodin (1:500, Chemicon). Nuclei were counter stained with DAPI (1:1000, Chemicon). Fluorescence images were visualized with a Nikon 80i eclipse (Nikon, Japan) upright microscope and captured with the Nikon DS-Fi1 (Nikon, Japan) using two 20× and 40× objective lens. The confocal laser scanning microscope system (Leica TCS SP5) was also used to capture 3D images using a 63× objective lens (oil).

Results

Characterization of Polymer Surface

Femtosecond laser is a new class of laser that is able to transfer highly focused energy in femtosecond (~$10^{-15}$s) pulses for removal of materials mass. By changing the laser power, scan speed and scan pass, the microchannels with two desirable dimensions were machined onto a 10 mm×10 mm PLLA-PCL film. The feature pitches (the combination of groove and interval widths) were uniform in each sample. As shown in FIG. 5, 3D microchannel topography with lined structure on the top view (SEM images) and sinusoidal surface on the cross section (3D profiler images) was achieved on the flat 2D surface of raw material through femtosecond laser machining. The channels were fabricated at a predetermined width, depth, as well as interval distance.

Figure 6:
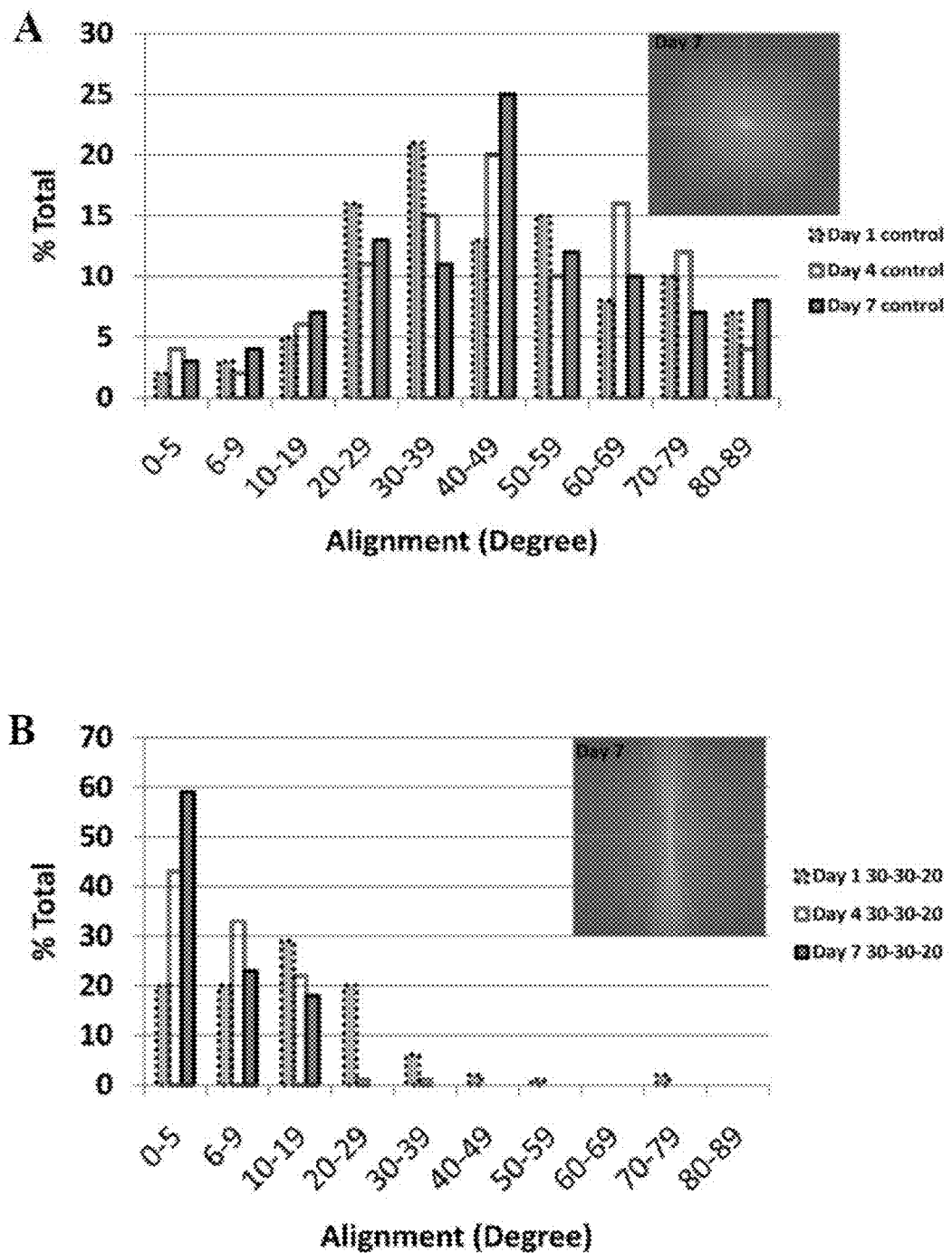
FIG. 6 shows alignment of adult human mesenchymal stem cells (hMSCs) on unpatterned (control) and laser micropatterned substrates. Quantitative study of cell orientation was done at Day 1, Day 4 and Day 7; Qualitative analysis using 2D FFT analysis was done at Day 7.
Figure 6:
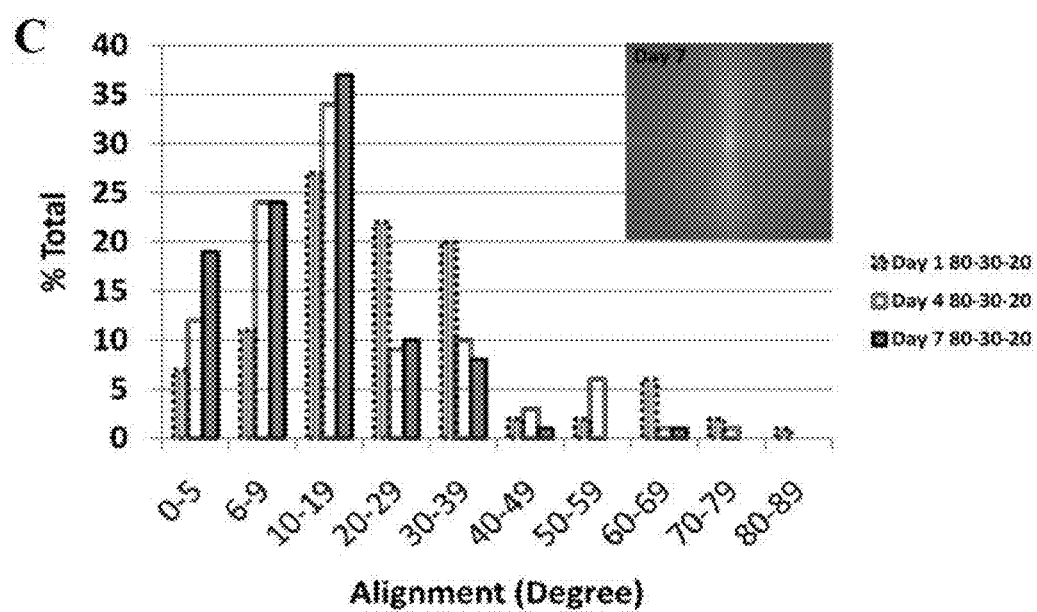

Cellular Organization hMSCs were cultured on the respective substrates (laser-machined substrates with dimensions 30-30-20, 80-30-20 and control without laser machining) for 1 day, 4 days, 7 days, 11 days and 14 days accordingly. To examine the cell morphology and microfilament arrangement, scaffolds with hMSCs were stained with phalloidin for F-actin and DAPI for nucleus. When hMSCs were cultured on the PLLA-PCL scaffolds with laser machined microchannels, both narrow and wide channels aided in cell elongation and cell alignment along the grating axis. In contrast, hMSCs cultured on controls showed no elongation or alignment in any specific direction. The quantitative and qualitative analysis of cell alignment on different substrates is shown in FIG. 6. For cells cultured on control, the cells were randomly oriented with degrees of alignment from 0-90° even when cells were becoming confluent (FIG. 6A). The cells cultured on scaffolds with narrow microchannels, 30-30-20, (FIG. 6B) have better alignment than that on the wider channels, 80-30-20 (FIG. 6C). This was observed from the beginning of cell growth on day 1. As seen in FIG. 6, for the narrower channel system (30-30-20), the angular distribution of the cells changed from a maximum at around 10-19 degree on day 4 to a maximum around 0-5 degree on day 7, clearly indicating progressively greater alignment of the cells along the grooved direction. This is not as evident in the wider channel substrate (80-30-20), where the preferred alignments continued to be in the 10-19 degree range regardless of the time of incubation. The cell alignment distribution on different surfaces after 7 days was also characterized by 2D FFT analysis, which converts spatial information into mathematically defined optical data. The 2D FFT frequency plot (FIG. 6 inset) depicting this data, represents the grayscale pixels distributed in patterns around the origin to reflect the degree of cell alignment.

Figure 7:
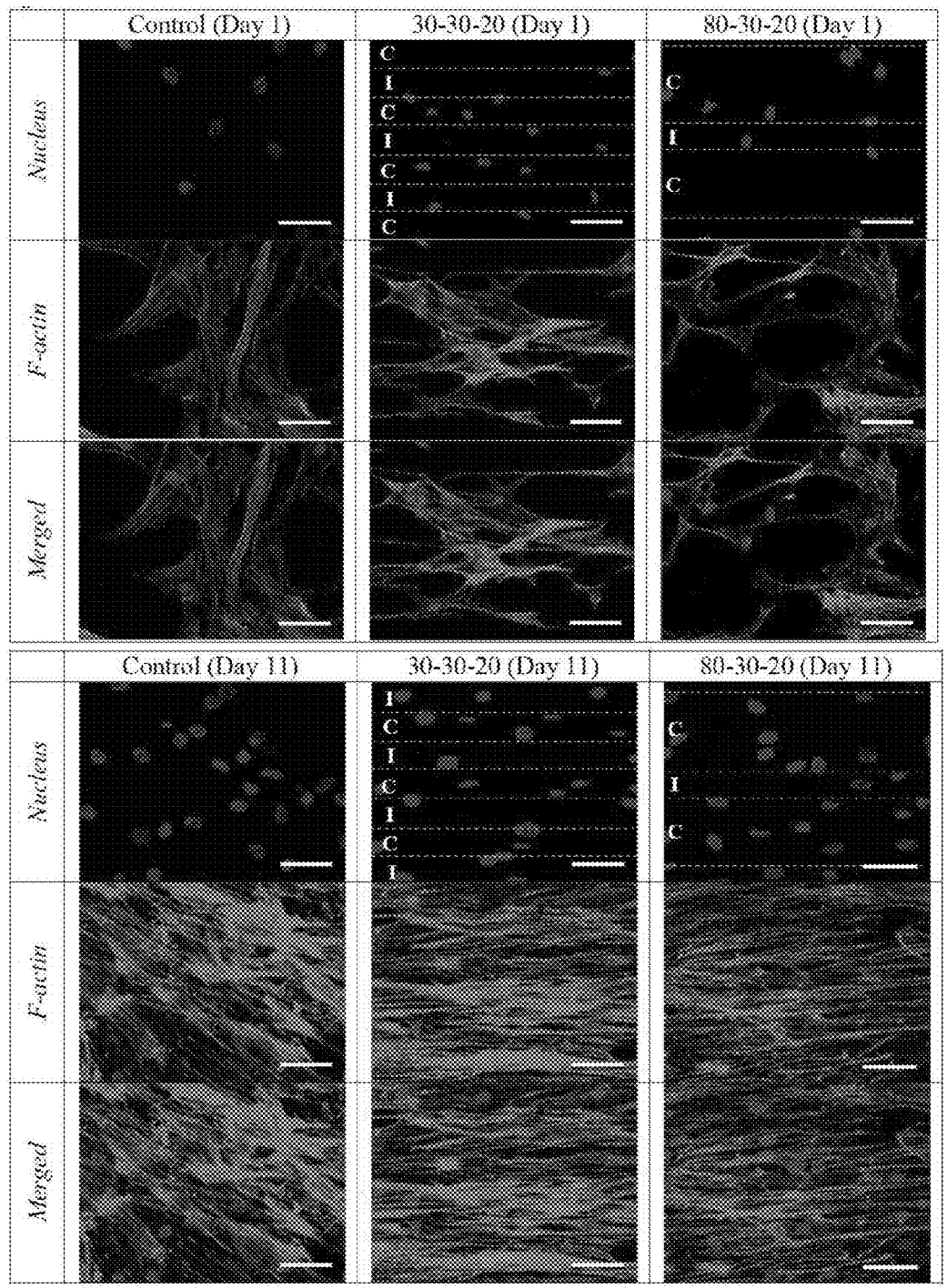
FIG. 7 shows phalloidin labeled F-actin (red), DAPI nuclear staining (blue) and merged fluorescent image for the non-patterned (left column) and micropatterned hMSCs (middle and right column). (C=channel, I=interval). Samples were cultured in DMEM for 1 day and 11 days before they were fixed and stained. All images were taken with a 63× objective lens (oil). (Scale bar, 50 μm).

From the results of phalloidin stained F-actin (FIG. 7), the unpatterned cells were well spread, with well-defined F-actin arranging circumferentially around the cell nucleus. Cell nucleus remained round after 11 days. Cells cultured on both laser micropatterned scaffolds experienced increased cellular alignment. The F-actin stress fibers, which were highly organized in bundles on the scaffolds with narrow microchannels, were stretched along the long axis of cells. The orientation of the stress fibers and the polarized elongated cell morphology on the scaffold with narrow microchannels, demonstrated good contact guidance.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numberical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

The invention claimed is:

1. An in vitro method for forming a tissue construct having a composite structure, comprising:
   (a) providing a biodegradable substrate in vitro, wherein the substrate is adapted to allow deposition or growth of a plurality of cells;
   (b) providing a vascularized layer in vitro, the vascularized layer comprising a plurality of blood vessels therein; and
   (c) adhering the vascularized layer to the biodegradable substrate in vitro.

2. The in vitro method of claim 1, wherein the plurality of blood vessels are formed by:
   (i) providing a plurality of biodegradable fibres;
   (ii) encapsulating the plurality of biodegradable fibres with cells selected from the group consisting of endothelial cells, smooth muscle cells, microvascular endothelial cells, stem cells, and combination thereof; and
   (iii) allowing the biodegradable fibres to degrade.

3. The in vitro method of claim 2, further comprising embedding the plurality of biodegradable fibers encapsulated with cells in a gel.

4. The in vitro method of claim 2, wherein encapsulating comprises culturing the biodegradable fibres with the cells in the presence of growth factors such as vascular endothelial growth factor (VEGF) medium.

5. The in vitro method of claim 2, wherein each of the substrate and the biodegradable fibres is independently selected from the group consisting of a polyglycolide, a polylactide, a polycaprolactone, a polyamide, an aliphatic polyester, a poly(ester amide), a poly(amino acid), a pseudo-poly(amino acid), a poly(lactide glycolide), poly(lactic acid ethylene glycol), poly(ethylene glycol), poly(ethylene glycol) diacrylate, a polyalkylene succinate, polybutylene diglycolate, polyhydroxybutyrate, polyhydroxyvalerate, a polyhydroxy-butyrate/polyhydroxyvalerate copolymer, poly(hydroxybutyrate-co-valerate), a polyhydroxyalkaoates, a poly(caprolactone-polyethylene glycol) copolymer, poly(valerolactone), a polyanhydride, a poly(orthoester), a poly-anhydride, a polyanhydride ester, poly(anhydride-co-imide), an aliphatic polycarbonate, a poly(hydroxyl-ester), a polydioxanone, a polycyanoacrylate, a poly(alkyl cyanoacrylate), a poly(amino acid), a poly(phosphazene), a poly-(propylene fumarate), poly(propylene fumarate-co-ethylene glycol), a poly(fumarate anhydride), a poly(propylene carbonate), fibrinogen, fibrin, gelatin, cellulose, a cellulose derivative, chitosan, alginate, a polysaccharide, starch, amylase, collagen, a polycarboxylic acid, a poly(ethyl ester-co-carboxylate carbonate), poly(iminocarbonate), poly(bisphenol A-iminocarbonate), poly(trimethylene carbonate), poly(ethylene oxide), poly(epsilon-caprolactone-dimethyltrimethylene carbonate), a poly(alkylene oxalate), a poly(alkylcarbonate), poly(adipic anhydride), a nylon copolyamide, carboxymethyl cellulose, a copoly(ether-ester), a polyether, a polyester, a polydihydropyran, a polyketal, a polydepsipeptide, a polyarylate, a poly(propylene fumarate-co-ethylene glycol), a hyaluronates, poly-p-dioxanone, a polyphosphoester, a polyphosphoester urethane, rayon, rayon triacetate, latex, and a composite thereof.

6. The in vitro method of claim 5, wherein the biodegradable fibres are poly(lactic-co-glycolic acid) (PLGA).

7. The in vitro method of claim 1, wherein the surface of the substrate is patterned to form a plurality of regions for the deposition or growth of the plurality of cells thereon.

8. The in vitro method of claim 7, wherein the substrate is further patterned to form a plurality of channels in the direction transverse to the substrate surface.

9. The in vitro method of claim 7, wherein the patterning of the substrate surface is formed by micro-contact printing, laser cutting, lithography or fibre spinning.

10. The in vitro method of claim 1, wherein the adhering comprises adhering the vascularized layer to the substrate via an intermediate layer.

11. The in vitro method of claim 10, wherein the intermediate layer is formed of gelatin, collagen or fibrin glue.

12. The in vitro method of claim 1, wherein the adhering comprises suturing the vascularized layer to the substrate.

13. A method, comprising:
   using an in vitro tissue construct having a composite structure that includes:
   (a) a biodegradable substrate adapted to allow deposition or growth of a plurality of cells; and
   (b) a vascularized layer comprising a plurality of blood vessels therein, wherein the using includes growing and structuring new tissue using the tissue construct or repairing damaged tissue using the tissue construct, wherein the vascularized layer is adhered to the biodegradable substrate.

* * * * *